United States Patent [19]
Yeh

[11] Patent Number: 5,423,779
[45] Date of Patent: Jun. 13, 1995

[54] HIGH EFFICIENCY FILTRATION PARTICULATE AND SMOKE EVACUATOR SYSTEM

[76] Inventor: Charles R. Yeh, 9800 Third Ct., SW., Plantation, Fla. 33324

[21] Appl. No.: 146,990

[22] Filed: Nov. 2, 1993

[51] Int. Cl.⁶ ............................................. A61M 1/00
[52] U.S. Cl. ..................................... 604/317; 55/487
[58] Field of Search ............................... 604/317–320; 55/486, 487; 422/171

[56] References Cited

U.S. PATENT DOCUMENTS

| | | | |
|---|---|---|---|
| 5,047,072 | 9/1991 | Wertz et al. | 55/1 |
| 5,288,469 | 2/1994 | Skalla | 422/171 |

Primary Examiner—Jerome L. Kruter
Attorney, Agent, or Firm—Rockey, Rifkin and Ryther

[57] ABSTRACT

The high efficiency filtration particulate and smoke evacuator of the present invention comprises a housing, a filtration means, a nozzle inlet and an air outlet. The filtration means includes a pre-filter to remove particles of intermediate size in conjunction with an odor filter. An ultra low penetration air filter is utilized (ULPA) to remove particles from the air flow down to particles of at least 0.01 microns or larger. Use of the ULPA filter helps to prevent the transmission of communicable diseases by limiting the size of unfilterable particulate matter.

6 Claims, 3 Drawing Sheets

HIGH EFFICIENCY FILTRATION PARTICULATE AND SMOKE EVACUATOR SYSTEM

BACKGROUND OF THE INVENTION

The present invention relates generally to filtering systems, and more particularly to filtering systems to be used with but separate from an electrosurgical device.

Apparatus which are useful to evacuate fluids and particulate matter from patients are known in the art, particularly in connection with medical and dental procedures. U.S. Pat. No. 2,784,717 to Thompson discloses an evacuative suction apparatus which is useful for evacuative dental purposes wherein a stream of water is sprayed onto the area being worked on. To evacuate and filter the waste water and material, Thompson '717 utilizes a flexible, perforate bag as the air filter means in an entrapment device which is interposed between a suction means and a fluid-conducting means.

U.S. Pat. No. 3,012,322 to Thompson discloses a dental and surgical evacuative suction apparatus similar to the '717 patent. The '322 patent to Thompson demonstrates the use of an entrapment device for the elimination of liquids and solids contained in the stream of air withdrawn from the mouth of a patient.

The utilization of lasers and electrosurgical devices are being utilized in surgical procedures by the medical community. Use of these techniques can lead to the production of smoke plume around the worksite on the patient, the smoke containing burning tissue fragments and micro-blood droplets containing live viruses such as HIV, HBV, HPV, etc. which can be released into the surrounding area and can cause problems for health care workers.

Filters and smoke evacuators of the prior art have not been generally suitable for removing and containing particulate matter generated during the use of such laser and electrosurgical devices. Some such devices commercially available are large, bulky equipment in which contaminants removed by means of various filters are not effectively contained. For example, such devices typically use canisters which when handled during the replacement of the filters, can come into contact with personnel changing the filter, thus potentially exposing health care workers to the contaminant thus removed.

Other such devices do not effectively and efficiently separate other such contaminants. As will be appreciated by those skilled in the art, effective containment of all tissue and bodily fluids is extremely important in light of the risk of transmission of communicable diseases.

It is thus an object of the present invention to provide a particulate and smoke evacuator which overcomes the disadvantages of the prior art.

It is a more specific object of the invention to provide a filtration and smoke evacuator apparatus which is highly efficient, which effectively contains particulate matter and bodily fluids with virtually no risk of exposure to health care workers and which has the ability to effectively separate substantially all known viruses.

It is another object of the present invention to provide a particulate and smoke evacuator apparatus which is relatively inexpensive, compact in size and can be conveniently mounted on the wall in physicians' offices without interfering with the use of other equipment commonly found there.

SUMMARY OF THE INVENTION

The concept of the present invention presides in a high efficiency system to filter particulate matter and to evacuate smoke which is highly efficient and which serves to remove substantially all known virus particulates. In the preferred embodiment of the invention, the system of the present invention comprises a compact housing sealed to prevent particulate matter and the like from entering the housing. Mounted in the housing is a removable filter cartridge consisting of the primary filter. In the preferred practice of the invention, the primary filter is a removable cartridge containing three filtration and/or adsorption components. The system of the present invention likewise includes a nozzle inlet means positioned adjacent the site of surgical activities into which the smoke and particulate matter are drawn under a reduced pressure. The inlet nozzle means is preferably mounted on a flexible conduit means, and preferably a pleated hose which serves to transmit particulate matter and smoke drawn into the nozzle inlet means to the filter where the particulate matter and smoke are removed. The air drawn in with the particulate matter and smoke can thus be exhausted through air outlet means after such air has been subjected to the action of the filter cartridge.

In the preferred practice of the invention, the nozzle inlet means includes a pre-filter to remove larger particulates from the particulate matter and smoke drawn in through the nozzle inlet means.

The system of the present invention thus constitutes an inexpensive and yet highly efficient apparatus for removing particulate matter, including viral particulates and smoke. The system is compact and can easily be mounted on the wall of a physician's office where it will not interfere with other equipment used by the physician.

DESCRIPTION OF A PREFERRED EMBODIMENT

Figure 1:
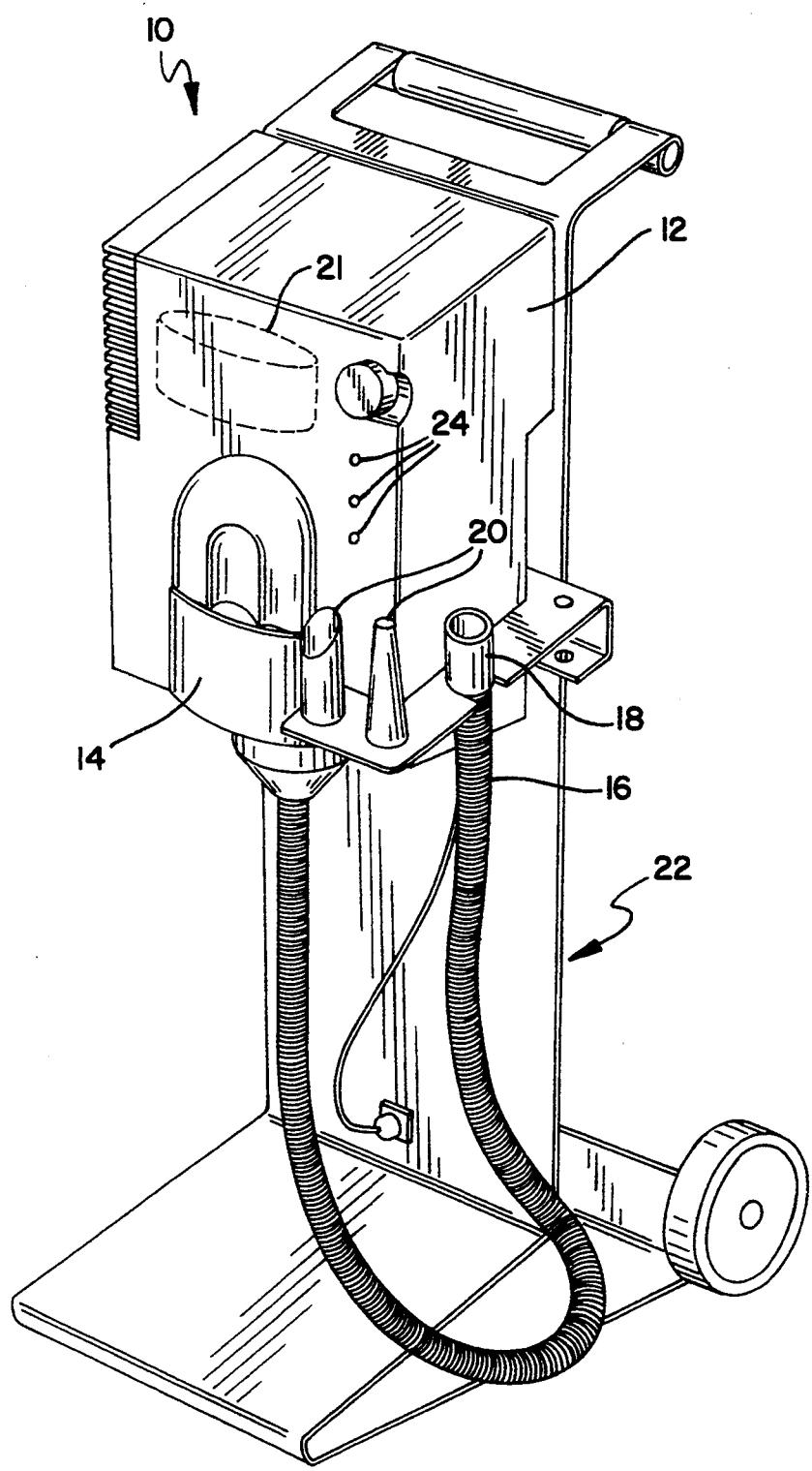
FIG. 1 is a perspective view of a high efficiency filtration particulate and smoke evacuator according to the present invention.

A preferred filtration and smoke evacuator system embodying the concepts of the present invention is shown in FIG. 1. As can be seen in that figure, the system 10 includes a sealed housing 12 on which there is mounted a filter cartridge 14. Attached to the filter cartridge 14 is a conduit means 16, preferably in the form of a pleated or corrugated hose which is flexible over its substantially entire length. Mounted on the end of the flexible conduit means 16 is a pre-filter means 18, preferably in the form of a pad of synthetic fibers such as polyester fibers. It will be understood, however, that various other pre-filters can be used, depending on the application. The pre-filter 18 is adapted to be fitted with one of a plurality nozzle 20. Thus, the nozzle 20 can be fitted on the pre-filter 18.

The housing 12 can be mounted on a wheel cart 22 as illustrated in FIG. 1. Alternatively, the housing can likewise be mounted directly on the wall of a physician's office or in a surgical suite so that it can be maintained out of the way of other equipment.

In the most preferred embodiment of the invention, the housing is equipped with means 24 for indicating that the primary filter should be replaced. As shown in FIG. 1, the means for indicating replacement of the filter can be in the form of a plurality of light emitting diodes to signal when the filter cartridge 14 should be changed.

Figure 2:
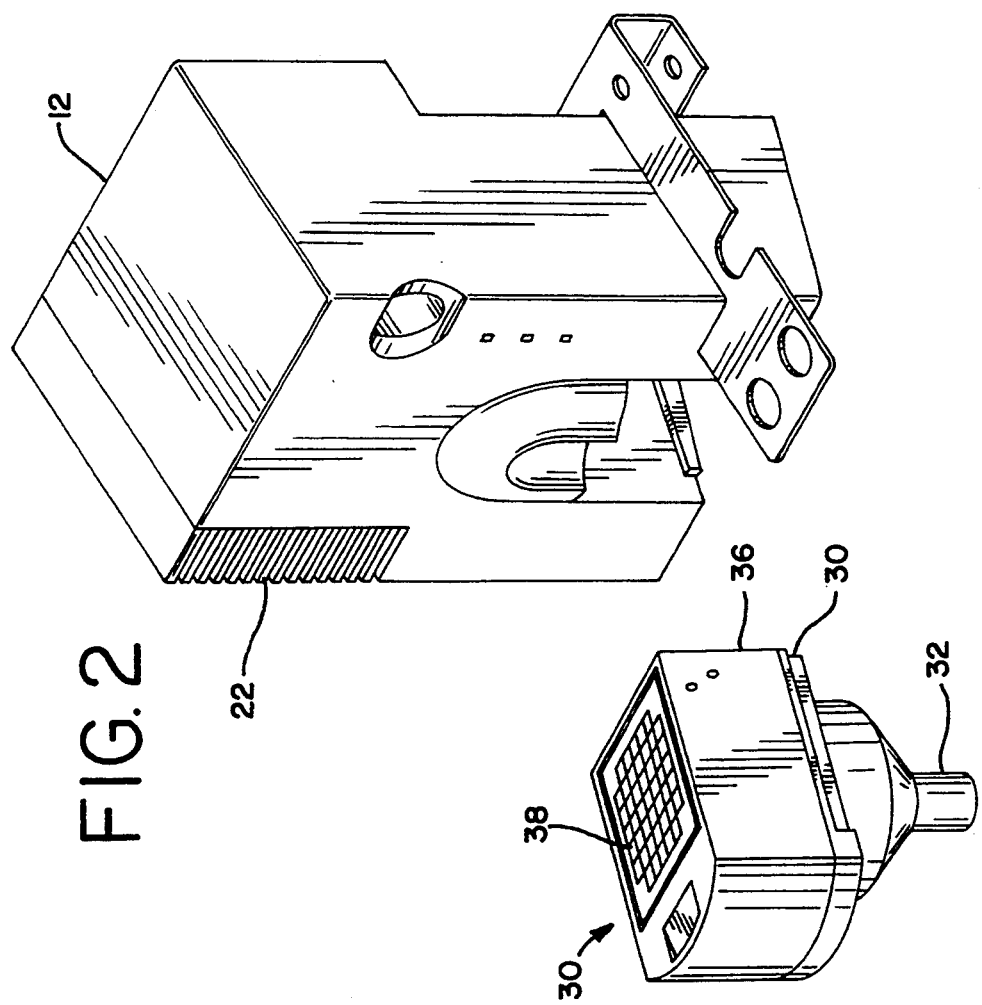
FIG. 2 is a perspective view of the filtration assembly which illustrates its connection to the housing.

The details of the housing and filter may be seen in FIG. 2 of the drawings. The housing 12 thus includes a center opening 26 in which the filter cartridge 14 is mounted by conventional mounting means. The housing also defines a clean air discharge means 28.

Figure 3:
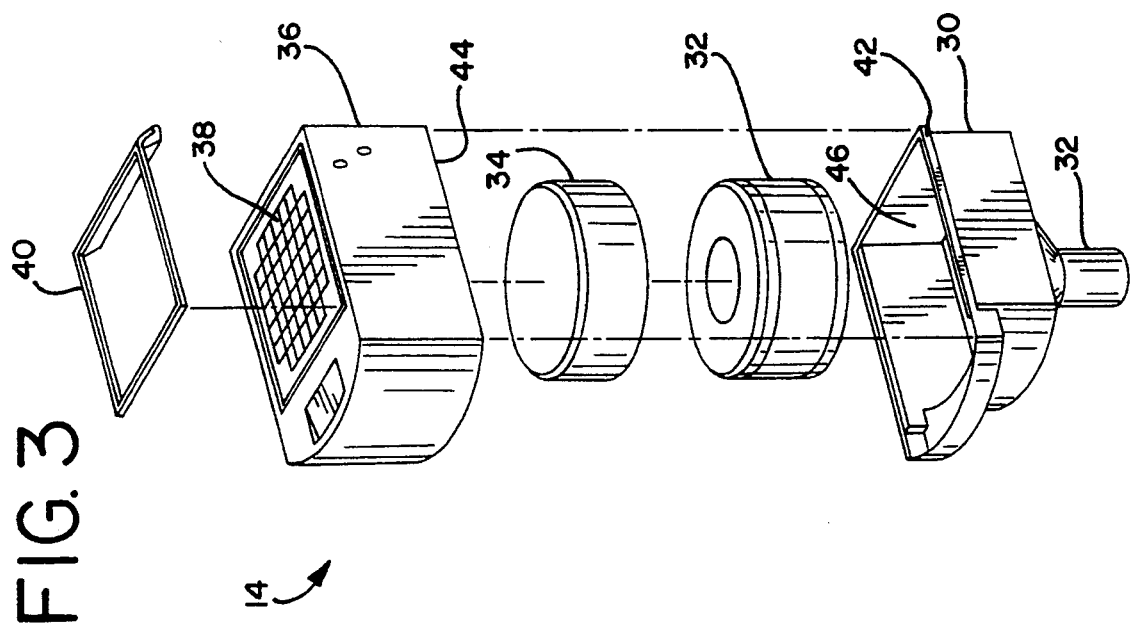
FIG. 3 is an exploded view of the filtration assembly for the evacuator of FIG. 1.

The details of the filter cartridge 14 is shown in FIG. 3 of the drawings, an exploded view of the cartridge 14. As can be seen in that drawing, the filter cartridge includes a base 30 having a generally cupped configuration with a fitting 32 at the base thereof adapted to be connected to the flexible conduit means 16. Mounted within the base 30 is a canister 32 containing an ultra low penetration air (ULPA) filter to remove particulates from the air flow having particulate sizes of 0.01 microns or higher. Thus, such filters, referred to in the art as ULPA, are commercially available and provide an efficiency rate of 99.99997 percent at 0.01 micron size. The ULPA filter used in the present invention is manufactured by ALFCO, a Division of AIR-MAZE. The use of the ULPA filters substantially prevents the transmission of communicable diseases by removable of substantially all aerosolized or airborne particulate matter generated by medical procedures using lasers or electrosurgical devices.

Positioned adjacent to the ULPA filter is an activated carbon filter 34 containing activated carbon to remove any contaminants not separated by the ULPA filter, most notably odor-containing gases.

The ULPA filter 32 and the activator carbon filter 34, both preferably in canister form, are sandwiched between the filter cartridge base 30 and the cartridge body member 36. If desired, it may be preferred, in some applications, to interpose between the cartridge body member 36 and the activated carbon cartridge 34 a final filter, such as a pad or mat of synthetic fibers such as polyester. The inclusion of that filter is not illustrated in FIG. 3 of the drawings. Finally, the cartridge body member 36 includes an air discharge grate 38, preferably provided with a gasket 40, through which air which has been filtered passes before being discharged through the air discharge 28. The housing thus defines passage means between the grate 38 and the air discharge means 28 for discharge of the clean gases to the atmosphere.

In the preferred practice of the invention, the filter can be changed by simply removing the entire cartridge 30 containing both the ULPA and activated carbon filters, as well as the cartridge body member 36 on the cartridge base 30, and new components inserted in their place. In that way, it is unnecessary for health care workers to come into contact with the contaminated canisters 32 and 34.

Thus, the cartridge base 30 and the cartridge body member 36 engage each other by means of flanges 42 and 44, respectively, thereby defining a cavity in which the ULPA filter and the activated carbon filter are positioned. Schematically illustrated in the drawing is a pump means 21 mounted above the grate 38 for applying a negative pressure or vacuum to the cavity defined by the filter cartridge base 30 and the cartridge body member 36. In that way, air is drawn through nozzle 20 fitted on the pre-filter 18 through the flexible conduit means 16 into the chamber 46. Liquid and solid contaminants are thus drawn through the nozzle 20, the pre-filter 18, and the flexible conduit 16 into the chamber 46. Particulate matter and liquid contaminants entrained in the air stream are first contacted with the ULPA filter 32; the filtered stream is then passed through the activated carbon filter 34. It has been found that best results are obtained when the ULPA filter precedes the activated carbon filter so that solid matter is filtered by the ULPA filter before the air stream containing liquid and particulate contaminants is passed to the activated carbon filters. It has been found that, by first passing the air stream with entrained contaminants through the ULPA filter, provides improved efficiency in the filtration of particulate viruses and the like.

Figure 4:
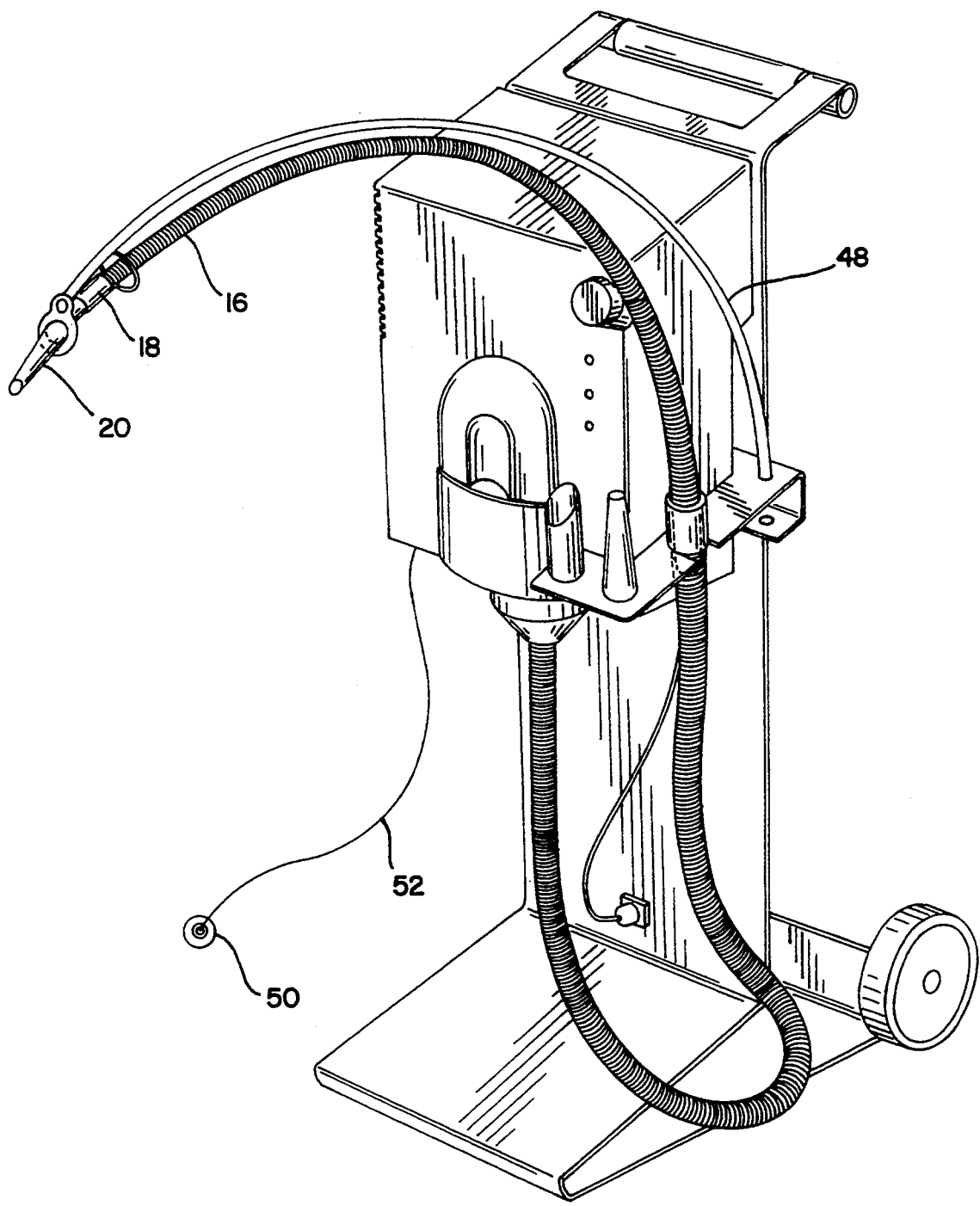
FIG. 4 is a perspective view of an alternative embodiment of the filtration assembly of the present invention.

An alternative embodiment of the present invention is shown in FIG. 4 of the drawing. This embodiment is like that shown in FIGS. 1 and 2, except that the preferred embodiment of FIG. 4 includes a boom 48 in the form of a flexible rod-like member which can be positioned in any desired manner. Mounted on the boom is the flexible conduit means 16 having a final filter 18 and a nozzle 20 mounted thereon. The boom can thus be positioned adjacent to the surgical site to evacuate particulate matter and smoke in a "hands free" operation. In addition, the device can be provided with a foot switch 50 and appropriate wiring 52 to allow the physician to turn on and off the particulate and smoke evacuator without having to use his or her hands.

It will be understood that various modifications and changes can be made in the details of construction and use without departing from the spirit of the invention, especially as defined by the following claims.

What is claimed is:

1. A particulate and smoke evacuator for filtering contaminated material from a human body comprising:
    (a) a compact housing having a center opening and exhaust means;
    (b) a removable filter cartridge positionable in said opening, said cartridge having a base and a body member defining a cavity therein and including an ultra low penetration air filter mounted on said base within said cavity for removing particulate matter having diameters of 0.01 microns or larger and an activated carbon filter positioned adjacent said ULPA filter within said cavity for removing odors, said base having a generally cupped configuration with a fitting at the bottom thereof;
    (c) a flexible conduit removably connected to said fitting;
    (d) a nozzle mounted on an end of said flexible conduit, said nozzle including a pre-filter for removing particulate matter and smoke; and
    (e) pump means positioned within said housing for causing a current of contaminated air to flow through said nozzle, said pre-filter and said flexible conduit to said filter cartridge whereby filtered air from said filter cartridge is expelled from said exhaust means in the housings,
    and whereby a new filter cartridge can be easily inserted in the housing to replace a contaminated filter.

2. An evacuator as defined in claim 1 which includes means on the housing to indicate replacement of the filter cartridge.

3. An evacuator as defined in claim 1 wherein the housing is adapted to be mounted on a wall.

4. An evacuator as defined in claim 1 wherein the pre-filter is a pad of synthetic fibers.

5. An evacuator as defined in claim 1 which includes a foot-activated switch for energizing and de-energizing said pump means.

6. An evacuator as defined in claim 1 which includes a boom mounted on said housing and adapted to secure the flexible conduit means in a pre-selected position.

* * * * *